United States Patent
Okamura

(10) Patent No.: US 7,073,941 B2
(45) Date of Patent: Jul. 11, 2006

(54) RADIOGRAPHIC APPARATUS AND RADIATION DETECTION SIGNAL PROCESSING METHOD

(75) Inventor: Shoichi Okamura, Nara (JP)

(73) Assignee: Shimadzu Corporation, Kyoto-fu (JP)

( * ) Notice: Subject to any disclaimer, the term of this patent is extended or adjusted under 35 U.S.C. 154(b) by 120 days.

(21) Appl. No.: 10/958,297

(22) Filed: Oct. 6, 2004

(65) Prior Publication Data

US 2005/0063508 A1    Mar. 24, 2005

(30) Foreign Application Priority Data

Oct. 8, 2003    (JP)    ............... 2003-349568

(51) Int. Cl.
*H05G 1/64* (2006.01)
*G01D 18/00* (2006.01)

(52) U.S. Cl. ............... 378/207; 378/19; 378/42; 378/91; 378/98.8; 250/367; 250/370.09; 250/370.11

(58) Field of Classification Search ............... 378/19, 378/42, 62, 91, 98.8, 207; 25/367–369, 361 C, 25/370.09, 370.11
See application file for complete search history.

(56) References Cited

U.S. PATENT DOCUMENTS

| | | | |
|---|---|---|---|
| 5,249,123 A | | 9/1993 | Hsieh |
| 5,265,013 A | * | 11/1993 | King et al. ............... 378/4 |
| 5,331,682 A | * | 7/1994 | Hsieh ............... 378/19 |
| 5,359,638 A | * | 10/1994 | Hsieh et al. ............... 378/4 |
| 5,517,544 A | | 5/1996 | Levinson |
| 5,644,610 A | * | 7/1997 | Crawford et al. ............... 378/19 |
| 6,067,342 A | * | 5/2000 | Gordon ............... 378/19 |
| 6,404,853 B1 | * | 6/2002 | Odogba et al. ............... 378/98.8 |
| 6,493,646 B1 | * | 12/2002 | Hsieh et al. ............... 378/19 |
| 6,920,198 B1 | * | 7/2005 | Xue et al. ............... 378/62 |
| 6,949,746 B1 | * | 9/2005 | Stierstorfer ............... 250/336.1 |
| 7,003,071 B1 | * | 2/2006 | Nagaoka et al. ............... 378/19 |

* cited by examiner

*Primary Examiner*—Allen C. Ho
(74) *Attorney, Agent, or Firm*—Rader, Fishman & Grauer PLLC

(57) ABSTRACT

An apparatus according to the invention includes a response coefficient to dose relationship memory for storing, in advance, a relationship of correspondence between intensities of an exponential function for impulse response and X-ray doses. The intensities of the exponential function determine conditions relating to an impulse response in a recursive computation performed to remove lag-behind parts from X-ray detection signals outputted from an FPD, thereby to obtain corrected X-ray detection signals. An impulse response coefficient setter sets an impulse response coefficient corresponding to an X-ray dose for an object under examination based on the relationship of correspondence between intensities of the exponential function and radiation doses. A time lag remover performs the recursive computation for time lag removal, with the intensity of an exponential function set to correspond to the X-ray dose for the object under examination. Thus, a lag-behind part is removed properly from each X-ray detection signal.

20 Claims, 7 Drawing Sheets

Fig.10

| X-ray dose W | intensity of exponential function $\alpha_n$ |
|---|---|
| $W_1$ | $\alpha_{n1}$ |
| $W_2$ | $\alpha_{n2}$ |
| $W_3$ | $\alpha_{n3}$ |
| ⋮ | ⋮ |
| ⋮ | ⋮ |
| $W_{m-2}$ | $\alpha_{n(m-2)}$ |
| $W_{m-1}$ | $\alpha_{n(m-1)}$ |
| $W_m$ | $\alpha_{nm}$ |

RADIOGRAPHIC APPARATUS AND RADIATION DETECTION SIGNAL PROCESSING METHOD

BACKGROUND OF THE INVENTION (1) Field of the Invention

This invention relates to a radiographic apparatus for medical or industrial use and a radiation detection signal processing method, for obtaining radiographic images based on radiation detection signals fetched at predetermined sampling time intervals by a signal sampling device from a radiation detecting device as radiation is emitted from a radiation emitting device. More particularly, the invention relates to a technique for eliminating time lags, due to the radiation detecting device, of the radiation detection signals taken from the radiation detecting device.

(2) Description of the Related Art

In a medical fluoroscopic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, in the fluoroscopic apparatus, X-ray detection signals for one X-ray image are taken at sampling time intervals from the FPD as a patient is irradiated with X rays from the X-ray tube. The fluoroscopic apparatus is constructed to obtain, based on the X-ray detection signals, an X-ray image corresponding to an X-ray penetration image of the patient for every period between sampling intervals. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals $\Delta t$.

That is, in the above U.S. patent, a lag-behind part included in each of the radiation detection signals taken at the sampling time intervals is assumed due to an impulse response formed of a plurality of exponential functions, and the following equation is used to derive radiation detection signal $x_k$ with a lag-behind part removed from radiation detection signal $y_k$:

$$x_k = [y_k - \Sigma_{n=1}^N \{\alpha_n \cdot [1-\exp(T_n)] \cdot \exp(T_n) \cdot S_{nk}\}]/\Sigma_{n=1}^N \beta_n$$

in which $T_n = -\Delta t/\tau_n$, $S_{nk} = x_{k-1} + \exp(T_n) \cdot S_{n(k-1)}$, and $\beta_n = \alpha_n \cdot [1-\exp(T_n)]$, where $\Delta t$: sampling intervals;
  k: subscript representing a k-th point of time in a sampling time series;
  N: the number of exponential functions with different time constants forming the impulse response;
  n: subscript representing one of the exponential functions forming the impulse response;
  $\alpha_n$: intensity of exponential function n; and
  $\tau_n$: attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. It has been confirmed that the time lag due to the FPD is not eliminated.

Further, U.S. Pat. No. 5,517,544 discloses a different proposal to solve the problem of the time lag caused by the FPD in acquiring CT images. This technique assumes a time lag of the FPD to be approximated by one exponential function, and removes a lag-behind part from a radiation detection signal by computation. Inventors herein have carefully reviewed the computation technique proposed in this U.S. patent. It has been found, however, that it is impossible for one exponential function to approximate the time lag of the FPD, and the time lag is not eliminated by this technique, either.

SUMMARY OF THE INVENTION

This invention has been made having regard to the state of the art noted above, and its object is to provide a radiographic apparatus and a radiation detection signal processing method for accurately eliminating time lags, due to a radiation detecting device, of radiation detection signals taken from the radiation detecting device.

The following technique is conceivable to eliminate time lags of the FPD fully. Specifically, in dealing with the time lags of the FPD, this technique removes a lag-behind part due to an impulse response based on the following recursive equations A-C:

$$X_k = Y_k - \Sigma_{n=1}^N \{\alpha_n \cdot [1-\exp(T_n)] \cdot \exp(T_n) \cdot S_{nk}\} \qquad A$$

$$T_n = -\Delta t/\tau_n \qquad B$$

$$S_{nk} = X_{k-1} + \exp(T_n) \cdot S_{n(k-1)} \qquad C$$

where $\Delta t$: the sampling time interval;
  k: a subscript representing a k-th point of time in a sampling time series;
  $Y_k$: an X-ray detection signal taken at the k-th sampling time;
  $X_k$: a corrected X-ray detection signal with a lag-behind part removed from the signal $Y_k$;
  $X_{k-1}$: a signal $X_k$ taken at a preceding point of time;
  $S_{n(k-1)}$: an $S_{nk}$ at a preceding point of time;
  exp: an exponential function;
  N: the number of exponential functions with different time constants forming the impulse response;
  n: a subscript representing one of the exponential functions forming the impulse response;
  $\alpha_n$: an intensity of exponential function n;
  $\tau_n$: an attenuation time constant of exponential function n; and
  when k=0, $X_0$=0 and $Sn_0$=0.

However, the technique proposed above, although capable of eliminating time lags to a considerable extent, falls short of accurately eliminating the time lags of the FPD. Inventors herein continued their research to achieve a further improvement.

For the recursive computation proposed by the above technique, impulse response coefficients N, $\alpha_n$ and $\tau_n$ specifying conditions relating to the impulse response are determined in advance. With the coefficients fixed, X-ray detection signal $Y_k$ is applied to equations A-C, thereby obtaining a lag-free X-ray detection signal $X_k$. In this case, if the radiation detection signal $Y_k$ is the same, the impulse response corresponding to the time lag included in the radiation detection signal also is fixed.

However, with an actual FPD, the impulse response corresponding to the time lag is not fixed. Inventors carried out experiments under various conditions for the cause of the impulse response not being fixed, and attained the following findings. That is, it has been found that the impulse response is variable with the exposure dose of radiation (e.g. X rays). FIG. 6 is a view schematically showing the findings, in which the horizontal axis represents exposure dose W of radiation and the vertical axis intensity $\alpha_n$ of exponential function n. The other impulse response coefficients N and $\tau_n$ are fixed. It will be seen from FIG. 6 that, when the exposure dose of radiation changes, intensity an of the exponential function also changes accordingly.

When $\alpha_n$ and N are fixed, $\tau_n$ changes with the exposure dose of radiation. When $\alpha_n$ and $\tau_n$ are fixed, N changes with the exposure dose of radiation. Since the exposure dose of radiation changes frequently according to radiographic conditions, even with the same FPD, appropriate values of N, $\alpha_n$ and $\tau_n$ which are the impulse response coefficients will also change frequently. Thus, it has been found that suitable values of the impulse response coefficients are changeable with the exposure dose of radiation.

Research has been continued on the above findings. A relationship between the impulse response coefficients specifying conditions relating to the impulse response in the recursive computation for removing time lags, and the exposure doses of radiation, is determined and stored in advance. An impulse response coefficient corresponding to a dose of radiation emitted to an object under examination is set according to the relationship between the impulse response coefficients and the exposure doses of radiation. Based on the set impulse response coefficient, the recursive computation is carried out to remove a lag-behind part from each radiation detection signal. Then, the lag-behind part may be removed accurately. These are the conclusive findings reached as a result of the research.

Based on the above findings, this invention provides a radiographic apparatus having a radiation emitting device for emitting radiation toward an object under examination, a radiation detecting device for detecting radiation transmitted through the object under examination, and a signal sampling device for taking radiation detection signals from the radiation detecting device at predetermined sampling time intervals, for obtaining radiographic images based on the radiation detection signals outputted from the radiation detecting device at the predetermined sampling time intervals as radiation is emitted to the object under examination, the apparatus comprising:

a time lag removing device for removing lag-behind parts from the radiation detection signals by a recursive computation, on an assumption that a lag-behind part included in each of the radiation detection signals taken at the predetermined sampling time intervals is due to an impulse response formed of a single exponential function or a plurality of exponential functions with different attenuation time constants;

a response coefficient to dose relationship storage device for storing, in advance, a relationship of correspondence between impulse response coefficients, which determine conditions relating to the impulse response in the recursive computation performed by the time lag removing device, and radiation doses; and an impulse response coefficient setting device for setting an impulse response coefficient corresponding to a radiation dose for the object under examination based on the relationship of correspondence between impulse response coefficients and radiation doses stored in the response coefficient to dose relationship storage device;

wherein the time lag removing device is arranged to obtain corrected radiation detection signals by performing the recursive computation based on the impulse response coefficient set by the impulse response coefficient setting device, to remove the lag-behind parts from the radiation detection signals.

With the radiographic apparatus according to this invention, radiation detection signals are outputted from the radiation detecting device at predetermined sampling time intervals as radiation is emitted from the radiation emitting device to an object under examination. A lag-behind part included in each of the radiation detection signals is regarded as due to an impulse response formed of a single exponential function or a plurality of exponential functions with different attenuation time constants. The time lag removing device removes such lag-behind parts by recursive computation as follows. The impulse response coefficient setting device sets an impulse response coefficient corresponding to a radiation dose for the object under examination based on the relationship of correspondence between impulse response coefficients, which determine conditions relating to the impulse response in the recursive computation performed by the time lag removing device, and radiation doses, stored in the response coefficient to dose relationship storage device. The recursive computation is performed based on the impulse response coefficient set as above, to remove a lag-behind part from each of the radiation detection signals. A radiographic image is created from corrected radiation detection signals thereby obtained.

Corrected radiation detection signals are derived from the recursive computation performed by the time lag removing device to remove the lag-behind parts from the radiation detection signals as described above. The response coefficient to dose relationship storage device stores, in advance, the relationship of correspondence between impulse response coefficients, which determine conditions relating to the impulse response in the recursive computation for time lag removal, and radiation doses. The impulse response coefficient setting device sets an impulse response coefficient corresponding to a radiation dose for the object under examination based on the relationship of correspondence between impulse response coefficients and radiation doses. The recursive computation for time lag removal is performed, with the impulse response coefficient set to correspond to the radiation dose for the object under examination. Thus, a lag-behind part is removed accurately from each X-ray detection signal.

Examples of the above relationship of correspondence between impulse response coefficients and radiation doses include the following.

The response coefficient to dose relationship storage device is arranged to store, in advance, and as the relationship of correspondence between impulse response coefficients and radiation doses, at least one of a relationship of correspondence between intensities of the exponential function as impulse response coefficients and radiation doses, a relationship of correspondence between attenuation time constants of exponential functions as impulse response coefficients and radiation doses, and a relationship of correspondence between numbers of exponential functions as impulse response coefficients and radiation doses.

In this case, at least one of the intensities of the exponential function, the attenuation time constants (hereinafter called simply "time constants" as appropriate) of exponential functions and the numbers of exponential functions is set to a value corresponding to the radiation dose, based on at least one of the relationship of correspondence between intensities of the exponential function as impulse response coefficients and radiation doses, the relationship of correspondence between time constants of the exponential functions as impulse response coefficients and radiation doses, and the relationship of correspondence between numbers of exponential functions as impulse response coefficients and radiation doses stored in advance in the response coefficient to dose relationship storage device.

In the above radiographic apparatus, preferably, the time lag removing device is arranged to perform the recursive computation for removing the lag-behind part from each of the radiation detection signals, based on the following equations A-C:

$$X_k = Y_k - \Sigma_{n=1}^{N} \{\alpha_n \cdot [1-\exp(T_n)] \cdot \exp(T_n) \cdot S_{nk}\} \quad A$$

$$T_n = -\Delta t / \tau_n \quad B$$

$$S_{nk} = X_{k-1} + \exp(T_n) \cdot S_{n(k-1)} \quad C$$

where $\Delta t$: the sampling time interval;
k: a subscript representing a k-th point of time in a sampling time series;
$Y_k$: an X-ray detection signal taken at the k-th sampling time;
$X_k$: a corrected X-ray detection signal with a lag-behind part removed from the signal $Y_k$;
$X_{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;
$\alpha_n$: an intensity of exponential function n; and
$\tau_n$: an attenuation time constant of exponential function n; and
when k=0, $X_0$=0 and $Sn_0$=0.

Where the recursive computation for removing the lag-behind part from each of the radiation detection signals is based on equations A-C, the corrected, lag-free X-ray detection signal $X_k$ may be derived promptly from equations A-C constituting a compact recurrence formula.

In the radiographic apparatus, for example, the impulse response coefficients may include intensities of the exponential function, the relationship of correspondence between intensities of the exponential function as impulse response coefficients and radiation doses being derived from a plurality of radiation data actually acquired with conditions of the same irradiation time and gradually differing radiation doses.

In this case, the relationship of correspondence between intensities of the exponential function as impulse response coefficients and radiation exposure doses is derived from a plurality of radiation data actually acquired with conditions of the same irradiation time and gradually differing radiation doses. Thus, an accurate correspondence is secured between the intensities of the exponential function and the radiation doses.

In another example of the radiographic apparatus, the impulse response coefficients include intensities of the exponential function, and the impulse response has a plurality of exponential functions, the relationship of correspondence between intensities of the exponential function as impulse response coefficients and radiation doses being stored for each of the exponential functions.

In this case, since the impulse response has a plurality of exponential functions, the impulse response becomes more accurate. In addition, since the relationship of correspondence between intensities of the exponential function as impulse response coefficients and radiation doses is stored for each of the exponential functions, the intensity of each exponential function may be set with increased accuracy. As a result, the lag-behind part may be removed properly from each radiation detection signal.

In a further example of the radiographic apparatus, the impulse response coefficients include intensities of the exponential function, the relationship of correspondence between intensities of the exponential function as impulse response coefficients and radiation doses being expressed by the following functional equation:

$$\alpha_n = Q \cdot \log W + q$$

where W: X-ray dose;
Q: gradient of an approximation line indicating the relationship between intensity of the exponential function and X-ray dose; and
q: section of the approximation line indicating the relationship between intensities of the exponential function and X-ray doses.

In this case, the relationship of correspondence between intensities of the exponential function and radiation doses may easily be stored in the form of the concise functional expression "$\alpha_n = Q \cdot \log W + q$".

The gradient Q and the section q of the approximation line are derived as follows. A graph of $\alpha_n = Q \cdot \log W + q$ is plotted as a straight line, with the horizontal axis representing logW and the vertical axis representing $\alpha n$. The straight line is inclined with the gradient Q of the approximation line. The coordinates of a point on the vertical axis at which the straight line intersects with the vertical axis indicate the sections q of the approximation line.

In the radiographic apparatus, the response coefficient to dose relationship storage device may be a table memory for storing the relationship of correspondence between impulse response coefficients and radiation doses in table form.

In this case, the table memory stores the relationship of correspondence between impulse response coefficients and radiation doses in table form. The impulse response coefficient setting device checks a radiation dose inputted, against the table stored in the response coefficient to dose relationship storage device, and reads and sets an impulse response coefficient corresponding to the radiation dose inputted.

In the radiographic apparatus, one example of the radiation detecting device is a flat panel X-ray detector having numerous X-ray detecting elements arranged longitudinally and transversely on an X-ray detecting surface.

The radiographic apparatus according to this invention may be a medical apparatus, and an apparatus for industrial use as well. An example of medical apparatus is a fluoroscopic apparatus. Another example of medical apparatus is an X-ray CT apparatus. An example of apparatus for industrial use is a nondestructive inspecting apparatus.

In another aspect of the invention, a radiation detection signal processing method is provided for taking, at predetermined sampling time intervals, radiation detection signals generated by irradiating an object under examination, and performing a signal processing to obtain radiographic images based on the radiation detection signals outputted at the predetermined sampling time intervals, the method comprising the steps of:

removing lag-behind parts from the radiation detection signals by a recursive computation, on an assumption that a lag-behind part included in each of the radiation detection signals taken at the predetermined sampling time intervals is due to an impulse response formed of a single exponential function or a plurality of exponential functions with different attenuation time constants;

setting, prior to the above removing step, an impulse response coefficient corresponding to a radiation dose for the object under examination based on a relationship, stored in advance, of correspondence between impulse response coefficients, which determine conditions relating to the impulse response in the recursive computation, and radiation doses; and obtaining corrected radiation detection signals by performing the recursive computation, in the above removing step, based on the impulse response coefficient set in the above setting step, to remove the lag-behind parts from the radiation detection signals.

This radiation detection signal processing method allows the radiographic apparatus according to the invention to be implemented in an advantageous manner.

In the above radiation detection signal processing method, it is preferred that the recursive computation for removing the lag-behind part from each of the radiation detection signals is performed based on the following equations A-C:

$$X_k = Y_k - \sum_{n=1}^{N} \{\alpha_n \cdot [1 - \exp(T_n)] \cdot \exp(T_n) \cdot S_{nk}\} \quad \text{A}$$

$$T_n = -\Delta t / \tau_n \quad \text{B}$$

$$S_{nk} = X_{k-1} + \exp(T_n) \cdot S_{n(k-1)} \quad \text{C}$$

where $\Delta t$: the sampling time interval;
  k: a subscript representing a k-th point of time in a sampling time series;
  $Y_k$: an X-ray detection signal taken at the k-th sampling time;
  $X_k$: a corrected X-ray detection signal with a lag-behind part removed from the signal $Y_k$;
  $X_{k-1}$: a signal $X_k$ taken at a preceding point of time;
  $S_{n(k-1)}$: an $S_{nk}$ at a preceding point of time;
  exp: an exponential function;
  N: the number of exponential functions with different time constants forming the impulse response;
  n: a subscript representing one of the exponential functions forming the impulse response;
  $\alpha_n$: an intensity of exponential function n; and
  $\tau_n$: an attenuation time constant of exponential function n; and
  when k=0, $X_0$=0 and $S_{n0}$=0.

Where the recursive computation for removing the lag-behind part from each of the radiation detection signals is based on equations A-C, the radiographic apparatus which performs the recursive computation based on equations A-C may be implemented in an advantageous manner.

In one example of the radiation detection signal processing method, the impulse response coefficients include intensities of the exponential function, the relationship of correspondence between intensities of the exponential function as impulse response coefficients and radiation doses being derived from a plurality of radiation data actually acquired with conditions of the same irradiation time and gradually differing radiation doses.

Where the above-noted relationship is derived from a plurality of radiation data actually acquired with conditions of the same irradiation time and gradually differing radiation doses, the radiographic apparatus which derives the above-noted relationship from a plurality of radiation data actually acquired with conditions of the same irradiation time and gradually differing radiation doses may be implemented in an advantageous manner.

In another example of the radiation detection signal processing method, the impulse response coefficients include intensities of the exponential function, the relationship of correspondence between intensities of the exponential function as impulse response coefficients and radiation doses being expressed by the following functional equation:

$$\alpha_n = Q \cdot \log W + q$$

where W: X-ray dose;
  Q: gradient of an approximation line indicating the relationship between intensity of the exponential function and X-ray dose; and
  q: section of the approximation line indicating the relationship between intensities of the exponential function and X-ray doses.

Where the above-noted relationship is expressed by this functional equation, the radiographic apparatus with the above-noted relationship expressed by this functional equation may be implemented in an advantageous manner.

In a further example of the radiation detection signal processing method, the relationship of correspondence between impulse response coefficients and radiation doses is stored in table form in a table memory.

Where the above-noted relationship is stored in table form in a table memory, the radiographic apparatus with the above-noted relationship stored in table form in the table memory may be implemented in an advantageous manner.

Preferably, the radiation detection signal processing method further comprises a step of storing, in advance, the relationship of correspondence between impulse response coefficients and radiation doses.

This storing step may be executed in time of installation or routine adjustment of the apparatus.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 10 is a schematic view showing contents stored in a table memory acting as a response coefficient to dose relationship memory of an apparatus in the second embodiment of the invention.

DESCRIPTION OF THE PREFERRED EMBODIMENTS

Preferred embodiments of this invention will be described in detail hereinafter with reference to the drawings.

First Embodiment

Figure 1:
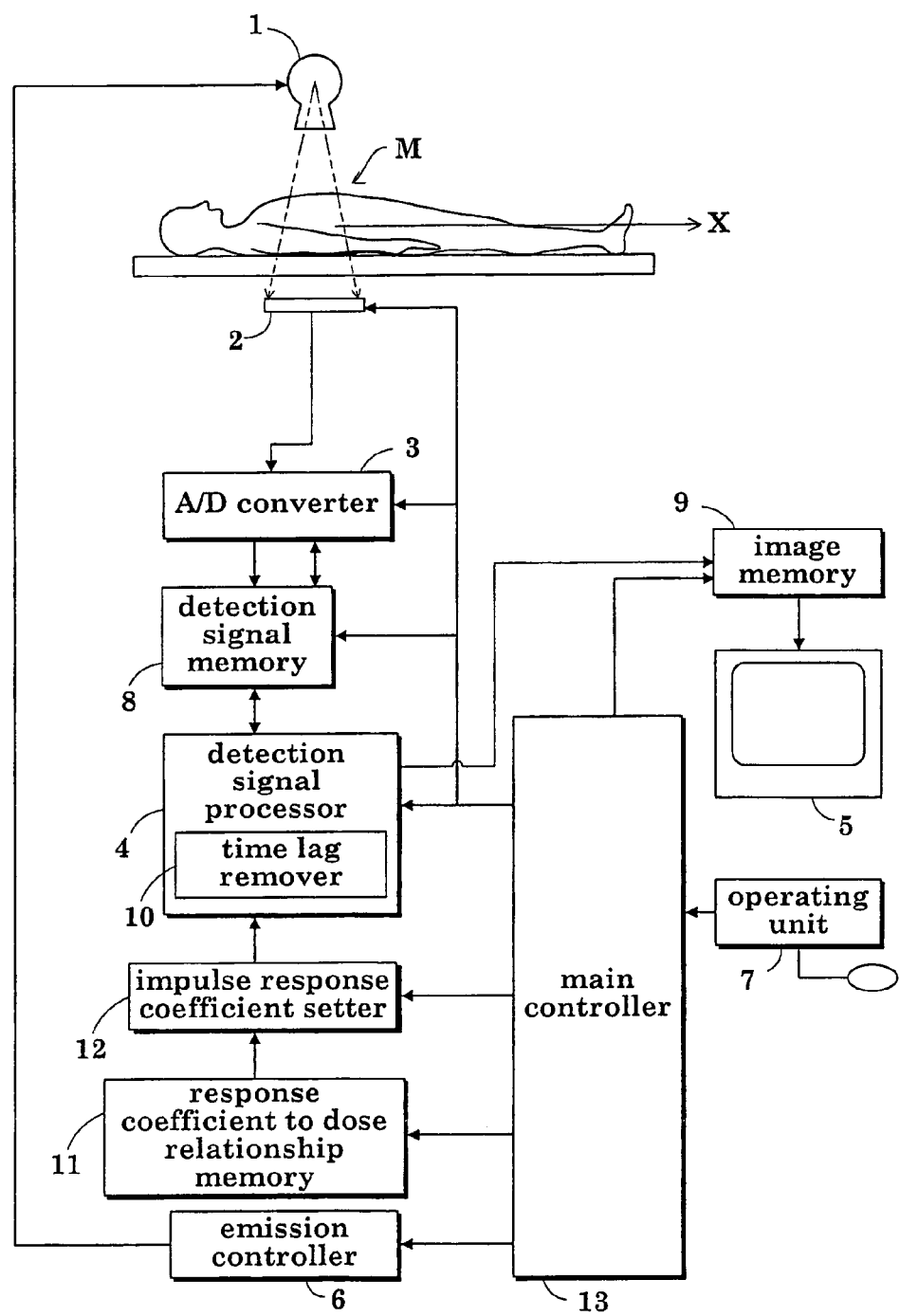
FIG. 1 is a block diagram showing an overall construction of a fluoroscopic apparatus in a first embodiment of the invention.

FIG. 1 is a block diagram showing an overall construction of a fluoroscopic apparatus in a first embodiment of this invention.

As shown in FIG. 1, the fluoroscopic apparatus includes an X-ray tube (radiation emitting device) 1 for emitting X rays toward a patient M, an FPD (radiation detecting device) 2 for detecting X rays transmitted through the patient M, an analog-to-digital converter 3 (signal sampling device) for digitizing X-ray detection signals (radiation detection signals) taken from the FPD (flat panel X-ray detector) 2 at predetermined sampling time intervals Δt, a detection signal processor 4 for creating X-ray images based on X-ray detection signals outputted from the analog-to-digital converter 3, and an image monitor 5 for displaying the X-ray images created by the detection signal processor 4. That is, the apparatus is constructed to acquire X-ray images from the X-ray detection signals taken from the FPD 2 by the analog-to-digital converter 3 as the patient M is irradiated with X rays, and display the acquired X-ray images on the screen of the image monitor 5. Each component of this apparatus will particularly be described hereinafter.

The X-ray tube 1 and FPD 2 are opposed to each other across the patient M. In time of X-ray radiography, the X-ray tube 1 is controlled by an emission controller 6 to emit X rays in the form of a cone beam to the patient M. At the same time, penetration X-ray images of the patient M produced by the X-ray emission are projected to an X-ray detecting surface of FPD 2.

The operator inputs irradiating conditions such as an X-ray dose through an operating unit 7, for example. The emission controller 6 controls the X-ray tube 1 according to the irradiating conditions inputted through the operating unit 7. X-ray doses are significantly different between an X-ray irradiation for continuous fluoroscopy and an X-ray irradiation for single-step radiography, for example.

Figure 2:
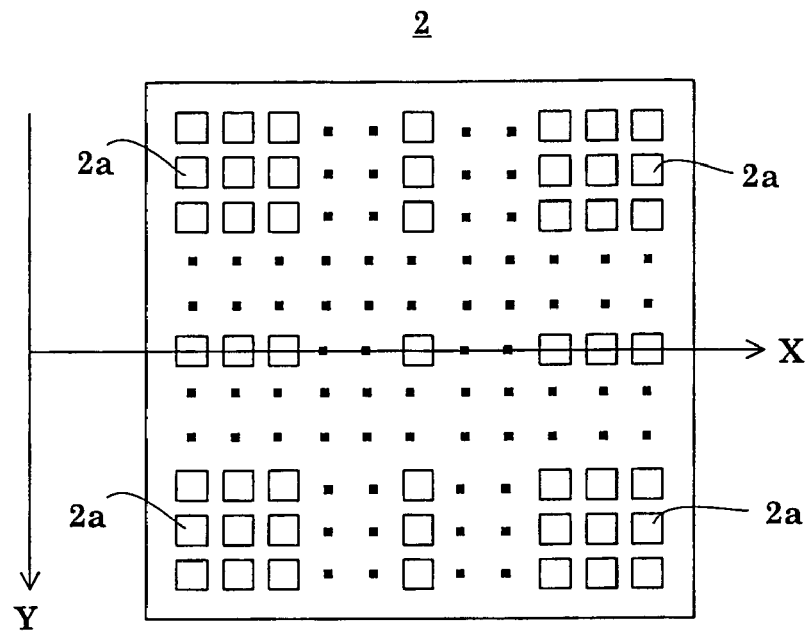
FIG. 2 is a plan view of an FPD used in the apparatus in the first embodiment.

As shown in FIG. 2, the FPD 2 has numerous X-ray detecting elements 2a arranged longitudinally and transversely along the direction X of the body axis of patient M and the direction Y perpendicular to the body axis, on the X-ray detecting surface to which penetration X-ray images from the patient M are projected. For example, X-ray detecting elements 2a are arranged to form a matrix of 1,536 by 1,536 on the X-ray detecting surface about 30 cm long and 30 cm wide. Each X-ray detecting element 2a of FPD 2 corresponds to one pixel in an X-ray image created by the detection signal processor 4. Based on the X-ray detection signals taken from the FPD 2, the detection signal processor 4 creates an X-ray image corresponding to a penetration X-ray image projected to the X-ray detecting surface.

Figure 3:
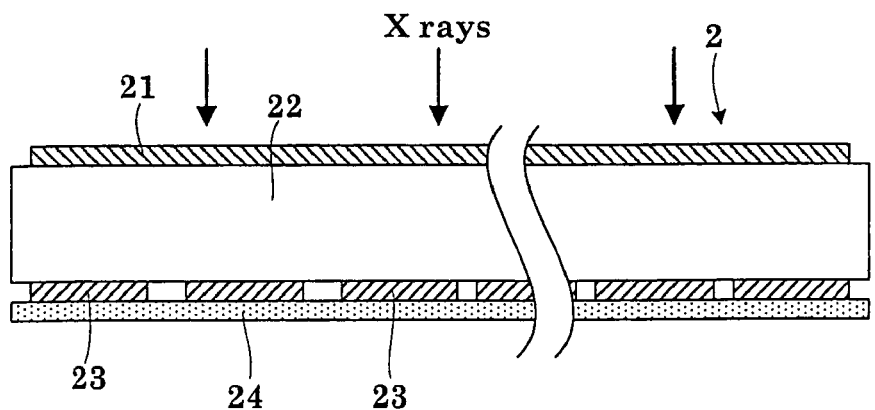
FIG. 3 is a sectional view of the FPD used in the apparatus in the first embodiment.

The FPD 2 has a construction in cross section as shown in FIG. 3. Specifically, the FPD 2 includes a semiconductor film 22 which is an X-ray induction film (e.g. amorphous Se thick film) for generating carriers in response to incident X rays, a bias voltage application electrode 21 disposed on the X-ray incidence surface of the semiconductor film 22, carrier collecting electrodes 23 which are part of X-ray detecting elements 2a of FPD 2 and disposed at the X-ray non-incidence surface of the semiconductor film 22, and a glass substrate 24 having the carrier collecting electrodes 23 deposited thereon. Further, the FPD 2 is constructed such that electric charges collected by the carrier collecting electrodes 23 are read by a storing and reading electric circuit (not shown) disposed on the glass substrate 24, and outputted through current-to-voltage converting amplifiers (not shown) and a multiplexer (not shown) to the analog-to-digital converter 3.

The analog-to-digital converter 3 continually takes X-ray detection signals for each X-ray image at sampling time intervals Δt, and stores the X-ray detection signals for X-ray image creation in a detection signal memory 8 disposed downstream of the converter 3. An operation for sampling (extracting) the X-ray detection signals is started before X-ray irradiation. X-ray images created by the detection signal processor 4 are transmitted to and stored in an image memory 9.

Figure 4:
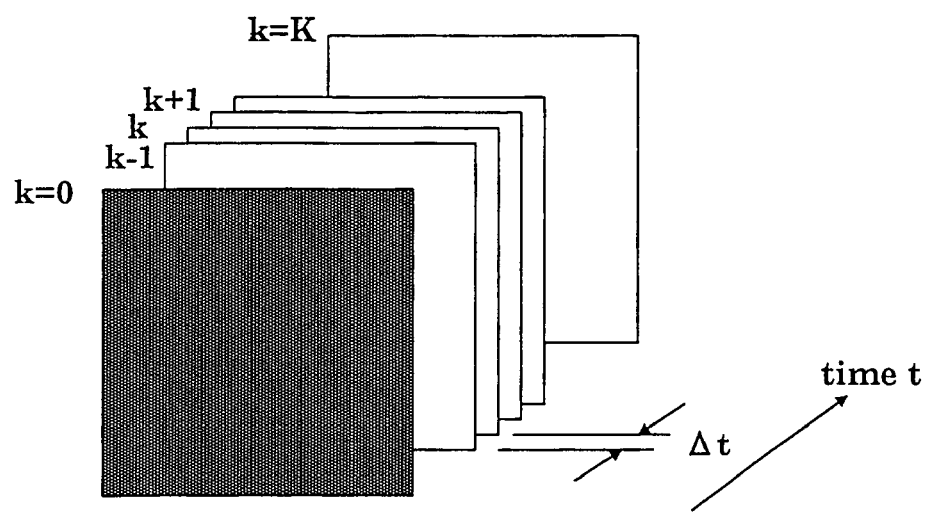
FIG. 4 is a schematic view showing a state of sampling X-ray detection signals during X-ray radiography by the apparatus in the first embodiment.

That is, as shown in FIG. 4, all X-ray detection signals for a penetration X-ray image are collected at each period between the sampling intervals Δt, and are successively stored in the detection signal memory 8. The sampling of X-ray detection signals by the analog-to-digital converter 3 before an emission of X rays may be started manually by the operator or automatically as interlocked with a command for X-ray emission.

As shown in FIG. 1, the fluoroscopic apparatus in the first embodiment includes a time lag remover (time lag removing device) 10 for computing corrected radiation detection signals free from time lags. A time lag is removed from each X-ray detection signal by a recursive computation based on an assumption that a lag-behind part included in each of the X-ray detection signals taken at the sampling time intervals Δt from the FPD 2 is due to an impulse response formed of a single exponential function or a plurality of exponential functions with different attenuation time constants.

Figure 5:
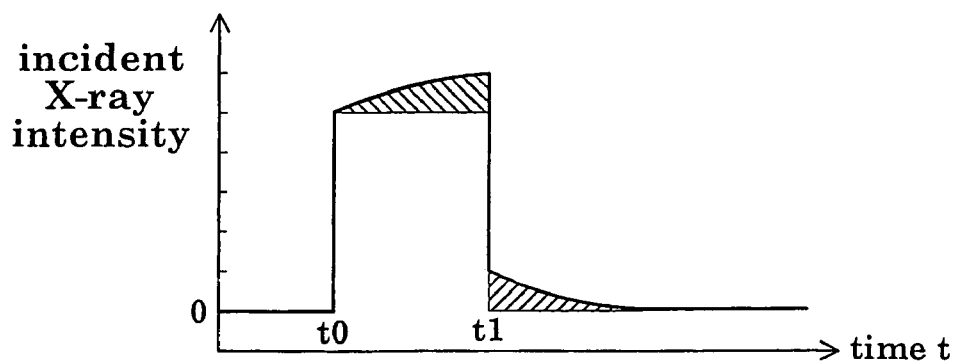
FIG. 5 is a signal waveform diagram showing a time lag in an X-ray detection signal.

With the FPD 2, an X-ray detection signal generated at each point of time, as shown in FIG. 5, includes signals corresponding to preceding X-ray emissions and remaining as a lag-behind part (hatched part). The time lag remover 10 removes this lag-behind part to produce a corrected, lag-free X-ray detection signal. Based on such lag-free X-ray detection signals, the detection signal processor 4 creates an X-ray image.

Specifically, the time lag remover 10 performs a recursive computation for removing a lag-behind part from each X-ray detection signal by using the following equations A-C:

$$X_k = Y_k - \Sigma_{n=1}^{N}\{\alpha_n \cdot [1-\exp(T_n)] \cdot \exp(T_n) \cdot \exp(S_{nk})\} \quad \text{A}$$

$$T_n = -\Delta t/\tau_n \quad \text{B}$$

$$S_{nk} = X_{k-1} + \exp(T_n) \cdot S_{n(k-1)} \quad \text{C}$$

where $\Delta t$: the sampling time interval;
  k: a subscript representing a k-th point of time in a sampling time series;
  $Y_k$: an X-ray detection signal taken at the k-th sampling time;
  $X_k$: a corrected X-ray detection signal with a lag-behind part removed from the signal $Y_k$;
  $X_{k-1}$: a signal $X_k$ taken at a preceding point of time;
  $S_{n(k-1)}$: an $S_{nk}$ at a preceding point of time;
  exp: an exponential function;
  N: the number of exponential functions with different time constants forming the impulse response;
  n: a subscript representing one of the exponential functions forming the impulse response;
  $\alpha_n$: an intensity of exponential function n; and
  $\tau_n$: an attenuation time constant of exponential function n; and
  when k=0, $X_0$=0 and $S_{n0}$=0.

The second term in equation A "$\Sigma_{n=1}^{N}\{\alpha_n \cdot [1-\exp(T_n)] \cdot \exp(T_n) \cdot S_{nk}\}$" corresponds to the lag-behind part. Thus, the apparatus in the first embodiment derives the corrected, lag-free X-ray detection signal $X_k$ promptly from equations A-C constituting a compact recurrence formula.

The apparatus in the first embodiment further includes a response coefficient to dose relationship memory (response coefficient to dose relationship storage device) 11 for storing, in advance, a relationship of correspondence between impulse response coefficients, which specify conditions relating to the impulse response in the recursive computation performed by the time lag remover 10, and X-ray doses, and an impulse response coefficient setter (impulse response coefficient setting device) 12 for setting an impulse response coefficient corresponding to an X-ray dose for the patient M based on the relationship of correspondence between impulse response coefficients and X-ray doses stored in the response coefficient to dose relationship memory 11. The time lag remover 10, as a characterizing feature thereof, performs a recursive computation based on the impulse response coefficient set by the impulse response coefficient setter 12, to remove a lag-behind part from each X-ray detection signal, thereby obtaining a corrected X-ray detection signal.

Figure 6:
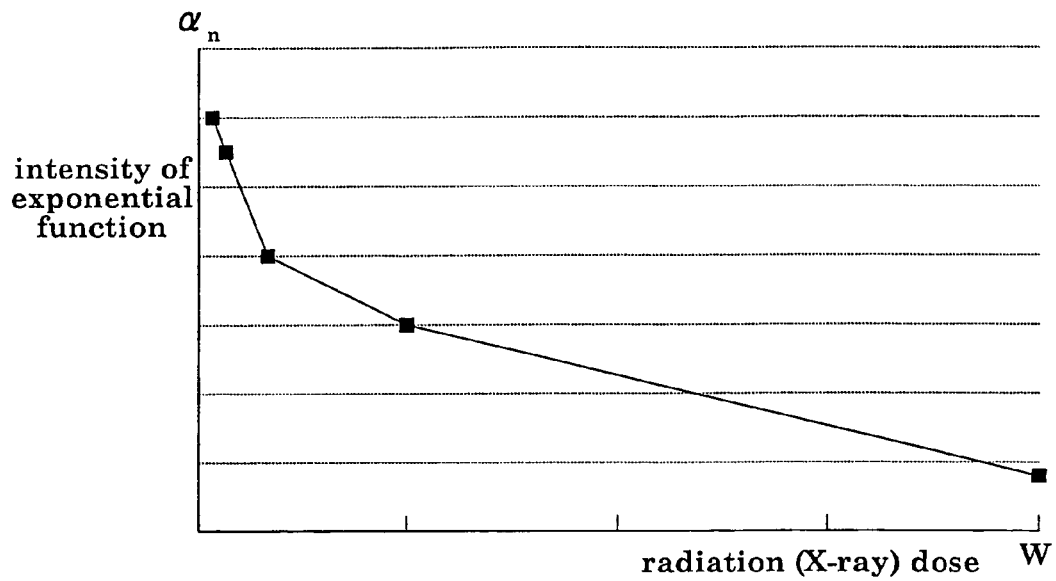
FIG. 6 is a graph showing a relationship between intensity of an exponential function serving as an impulse response coefficient and X-ray dose in the first embodiment.

As the relationship of correspondence between impulse response coefficients and X-ray doses, the response coefficient to dose relationship memory 11 stores, in advance, a relationship of correspondence between intensities of exponential functions as impulse response coefficients and X-ray doses. In the first embodiment, the relationship of correspondence between intensities of exponential functions as impulse response coefficients and X-ray doses stored in the response coefficient to dose relationship memory 11 is determined by measuring attenuation characteristics of X-ray detection signals of some X-ray images actually acquired with conditions of the same irradiation time and gradually differing X-ray doses. Specifically, for example, the intensity of an exponential function matching each X-ray image is determined based on images (radiation data) acquired with gradually differing X-ray doses. FIG. 6 shows a graph plotted with values of intensity $\alpha_n$ of the exponential function determined and X-ray doses W used in acquiring the X-ray images forming the basis for determining the values of intensity $\alpha_n$. The horizontal axis represents the X-ray dose, while the vertical axis represents the intensity of the exponential function. A functional expression showing a curve linking the plotted points is obtained as a relationship of correspondence between intensities of the exponential function and X-ray doses. The relationship of correspondence between intensities of the exponential function and X-ray doses determined is stored in the form of the functional expression in the response coefficient to dose relationship memory 11. The intensity $\alpha_n$ of the exponential function is proportional to the logarithm of X-ray dose W.

In order to carry out X-ray radiography with the same irradiation time, an input is made through the operating unit 7 to set a uniform X-ray pulse width for all times. In order to change the X-ray dose gradually, an input is made through the operating unit 7 to change gradually a tube current (mA) for the X-ray tube 1. At this time, the X-ray dose is changed at suitable intervals within a range that may be used (between maximum dose and minimum dose). When measuring the attenuation characteristics of X-ray detection signals of X-ray images, each X-ray image is picked up with a fixed irradiation time (e.g. 10 seconds) by using a phantom for the patient M. The relationship of correspondence between intensity of the exponential function and X-ray dose is obtained and stored, for example, in time of installation or routine adjustment of the apparatus.

With the apparatus in the first embodiment, as described above, the relationship of correspondence between intensities of the exponential function as impulse response coefficient and X-ray doses is obtained from a plurality of X-ray images actually picked up with the conditions of the same irradiation time and gradually changing X-ray doses, i.e. from actual images. Thus, the intensity of the exponential function and the X-ray dose may be in an accurately corresponding relationship.

The relationship of correspondence between intensity $\alpha_n$ of the exponential function as impulse response coefficient and X-ray dose W shown in FIG. 6 may be expressed by the following concise functional equation:

$$\alpha_n = Q \cdot \log W + q$$

where W: X-ray dose;
  Q: gradient of an approximation line indicating the relationship between intensity of the exponential function and X-ray dose; and
  q: section of the approximation line indicating the relationship between intensities of the exponential function and X-ray doses.

Figure 7:
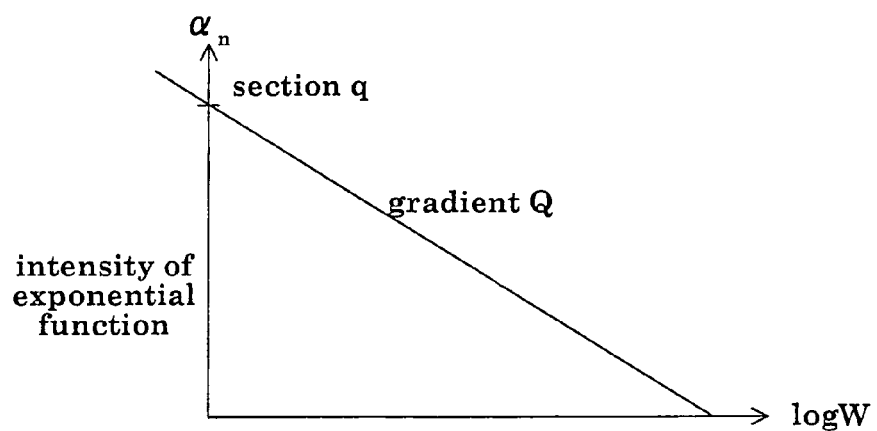
FIG. 7 is a graph showing, in an approximation line, the relationship between intensity of the exponential function serving as an impulse response coefficient and X-ray dose in the first embodiment.

The gradient Q and the section q of the approximation line are derived as follows. As shown in FIG. 7, $\alpha_n = Q \cdot \log W + q$ is plotted as a straight line on a graph with the horizontal axis representing logW and the vertical axis representing $\alpha_n$. The straight line is inclined with the gradient Q of the approximation line. The coordinates of a point on the vertical axis at which the straight line intersects with the vertical axis indicate the sections q of the approximation line.

With the apparatus in the first embodiment, therefore, the relationship of correspondence between intensity $\alpha_n$ of the exponential function as impulse response coefficients and the X-ray dose W may easily be stored in the form of the above concise functional expression in the response coefficient to dose relationship memory 11.

The apparatus in the first embodiment has a plurality of exponential functions constituting an impulse response. The relationship of correspondence between intensities of an exponential function as impulse response coefficient and X-ray doses is stored for each exponential function. The specific number of exponential functions may be two or three. That is, one functional expression, as noted above, is stored for each exponential function constituting an impulse response coefficient. For each function expression, the gradient Q and section q of the approximation line take suitable values, respectively.

Since an impulse response is formed of a plurality of exponential functions as noted above, the impulse response becomes more accurate. Further, since the relationship of correspondence between intensities of the exponential function as impulse response coefficients and X-ray doses is stored for each exponential function, the intensity of each exponential function may be set properly. As a result, a lag-behind part may be removed from each X-ray detection signal with increased accuracy.

The impulse response coefficient setter 12 sets each impulse response coefficient as follows. During X-ray radiography, for example, an X-ray dose is derived from the X-ray pulse width and tube current (mA) set through the operating unit 7, and then the X-ray dose derived is substituted into the expression $\alpha_n = Q \cdot \log W + q$. After determining the intensity of the exponential function corresponding to the X-ray dose used in the on-going X-ray radiography, the impulse response coefficient setter 12 sets this intensity of the exponential function as intensity of the exponential function for the recursive computation performed by the time lag remover 10.

On the other hand, the time lag remover 10 performs an recursive computation according to the impulse response coefficient set by the impulse response coefficient setter 12, and removes a lag-behind part from each X-ray detection signal.

In the first embodiment, the analog-to-digital converter 3, detection signal processor 4, emission controller 6, time lag remover 10, response coefficient to dose relationship memory 11 and impulse response coefficient setter 12 are operable on instructions and data inputted from the operating unit 7 or on various commands outputted from a main controller 13 with progress of X-ray radiography.

Figure 8:
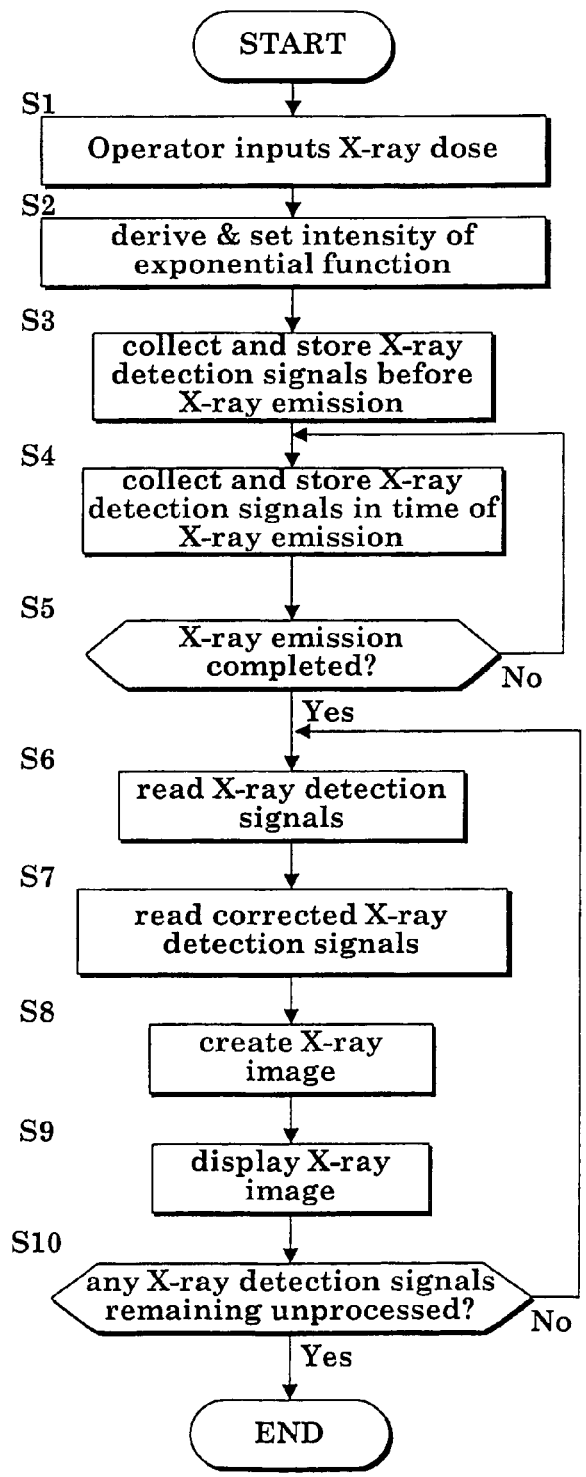
FIG. 8 is a flow chart showing a procedure of X-ray radiography by the apparatus in the first embodiment.

Next, an operation for performing X-ray radiography with the apparatus in the first embodiment will particularly be described with reference to the drawings. FIG. 8 is a flow chart showing a procedure of X-ray radiography by the apparatus in the first embodiment. It is assumed that the response coefficient to dose relationship memory 11 already stores the functional expression showing the relationship of correspondence between intensities of the exponential function and X-ray doses, and that the patient M is placed on a top board and set to a position for radiography.

[Step S1] The operator inputs radiographic conditions including an X-ray dose through the operating unit 7.

[Step S2] The impulse response coefficient setter 12 substitutes the X-ray dose set by the operator into the functional expression stored in the response coefficient to dose relationship memory 11, and derives and sets the intensity an of the exponential function corresponding to the X-ray dose set by the operator. In the first embodiment, a plurality of exponential functions constitute an impulse response, and therefore intensities of all the exponential functions are derived and set.

[Step S3] The analog-to-digital converter 3 starts taking X-ray detection signals Yk for one X-ray image from the FPD 2 at each period between the sampling time intervals $\Delta t (=1/30$ second) before X-ray emission. The X-ray detection signals taken are stored in the detection signal memory 8.

[Step S4] In parallel with a continuous or intermittent X-ray emission to the patient M initiated by the operator, the analog-to-digital converter 3 continues taking X-ray detection signals $Y_k$ for one X-ray image at each period between the sampling time intervals $\Delta t$ and storing the signals in the detection signal memory 8.

[Step S5] When the X-ray emission is completed, the operation proceeds to step S6. When the X-ray emission is uncompleted, the operation returns to step S4.

[Step S6] X-ray detection signals $Y_k$ for one X-ray image collected in one sampling sequence are read from the detection signal memory 8.

[Step S7] The time lag remover 10 performs the recursive computation based on the equations A-C, and derives corrected X-ray detection signals $X_k$, i.e. pixel values, with lag-behind parts removed from the respective X-ray detection signals $Y_k$.

In the first embodiment, the impulse response coefficient setter 12 sets a suitable value to the intensity of the exponential function of the impulse response coefficient according to the X-ray dose inputted by the operator. Predetermined suitable values are set to the number N of exponential functions of impulse response coefficients and to the time constant $\tau_n$ of the exponential functions, regardless of the X-ray dose.

[Step S8] The detection signal processor 4 creates an X-ray image from the corrected X-ray detection signals $X_k$ for one sampling sequence (for one X-ray image).

[Step S9] The X-ray image created is displayed on the image monitor 5.

[Step S10] When unprocessed X-ray detection signals $Y_k$ remain in the detection signal memory 8, the operation returns to step S6. When no unprocessed X-ray detection signals $Y_k$ remain, the X-ray radiography is ended.

In the first embodiment, the time lag remover 10 computes the corrected X-ray detection signals $X_k$ corresponding to the X-ray detection signals $Y_k$ for one X-ray image, and the detection signal processor 4 creates an X-ray image, both at sampling time intervals $\Delta t (=1/30$ second). That is, X-ray images may be created one after another at a rate of about 30 images per second, with the created X-ray images continuously displayed for a dynamic display of the X-ray images.

Next, the process of recursive computation carried out in step S7 in FIG. 8 by the time lag remover 10 will be described with reference to FIG. 9.

Figure 9:
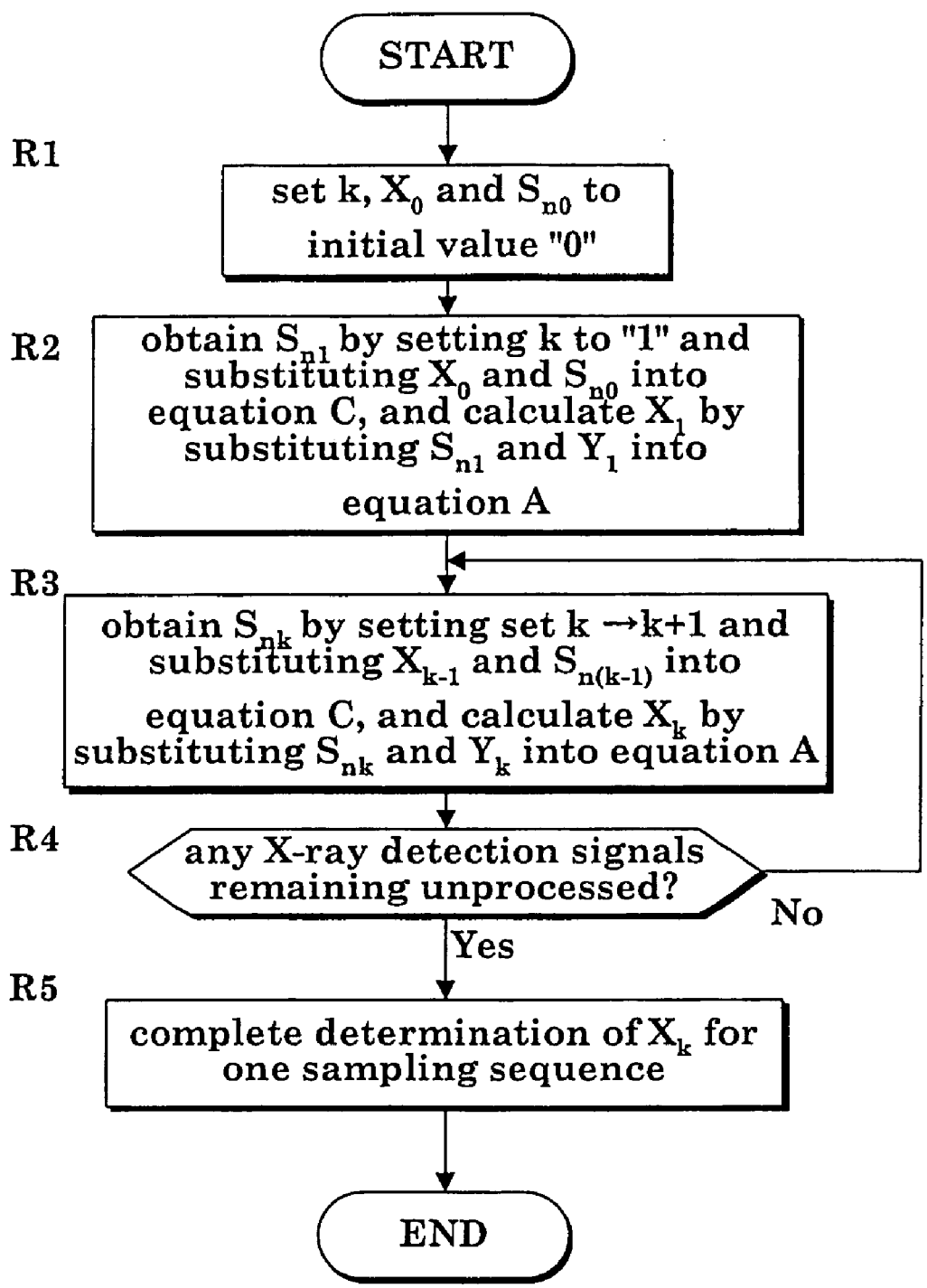
FIG. 9 is a flow chart showing a recursive computation process for time lag removal by the apparatus in the first embodiment.

FIG. 9 is a flow chart showing a recursive computation process for time lag removal carried out by the apparatus in the first embodiment.

[Step R1] A setting k=0 is made, and $X_0=0$ in equation A and $S_{n0}=0$ in equation C are set as initial values before X-ray emission. Where the number of exponential functions is 3 (N=3), $S_{10}$, $S_{20}$ and $S_{30}$ are all set to 0.

[Step R2] In equations A and C, k=1 is set. That is, $S_{11}$, $S_{21}$ and $S_{31}$ are derived from equation C, i.e. $S_{n1} = X_0 + \exp(T_n) \cdot S_{n0}$. Further, a corrected X-ray detection signal is obtained by substituting $S_{11}$, $S_{21}$ and $S_{31}$ derived and X-ray detection signal $Y_1$ into equation A.

[Step R3] After incrementing k by 1 (k=k+1) in equations A and C, $X_{k-1}$ of a preceding time is substituted into equation C, thereby obtaining $S_{1k}$, $S_{2k}$ and $S_{3k}$. Further, corrected X-ray detection signal $X_k$ is obtained by substituting $S_{1k}$, $S_{2k}$ and $S_{3k}$ derived and X-ray detection signal $Y_k$ into equation A.

[Step R4] When there remain unprocessed X-ray detection signals $Y_k$, the operation returns to step R3. When no unprocessed X-ray detection signals $Y_k$ remain, the operation proceeds to the next step R5.

[Step R5] Corrected X-ray detection signals $X_k$ for one sampling sequence (for one X-ray image) are obtained to complete the recursive computation for the one sampling sequence.

According to the apparatus in the first embodiment, as described above, the time lag remover 10 performs the recursive computation for time lag removal, after the impulse response coefficient setter 12 sets the intensity of the exponential function as an impulse response coefficient corresponding to the X-ray dose to the patient M. Thus, a lag-behind part is removed accurately from each X-ray detection signal. With the apparatus in the first embodiment, therefore, the time lags of the X-ray detection signals due to the FPD 2 may be removed properly from the X-ray detection signals fetched from the FPD 2.

Second Embodiment

In the fluoroscopic apparatus in the second embodiment, the response coefficient to dose relationship memory 11 is a table memory for storing the relationship of correspondence between intensity $\alpha_n$ of the exponential function as impulse response coefficient and X-ray dose W not in the form of the functional expression but in table form. The other aspects of the apparatus are the same as in the first embodiment, and will not be described again.

In the apparatus in the second embodiment, the table memory stores the relationship of correspondence between intensity $\alpha_n$ of the exponential function as impulse response coefficient and X-ray dose W in table form as shown in FIG. 10. The impulse response coefficient setter 12 checks an X-ray dose inputted by the operator against the table stored in the response coefficient to dose relationship memory 11, and reads and sets intensity $\alpha_n$ of the exponential function corresponding to the X-ray dose inputted by the operator.

With the apparatus in the second embodiment also, the time lag remover 10 performs the recursive computation for time lag removal, after the impulse response coefficient setter 12 sets the intensity of the exponential function as an impulse response coefficient corresponding to the X-ray dose to the patient M. Thus, a lag-behind part is removed accurately from each X-ray detection signal. With the apparatus in the second embodiment, therefore, the time lags of the X-ray detection signals due to the FPD 2 may be removed properly from the X-ray detection signals fetched from the FPD 2.

This invention is not limited to the foregoing embodiments, but may be modified as follows:

(1) In the embodiments described above, the response coefficient to dose relationship memory 11 stores the relationship of correspondence between intensities of the exponential function as impulse response coefficients and X-ray doses. Instead, the memory 11 may store a relationship of correspondence between time constant $\tau_n$ of the exponential function as impulse response coefficients and X-ray doses, or a relationship of correspondence between the number N of exponential functions as an impulse response coefficient and X-ray doses.

(2) The embodiments described above employ an FPD as the radiation detecting device. This invention is applicable also to an apparatus having a radiation detecting device other than an FPD that causes time lags in X-ray detection signals.

(3) While the apparatus in the foregoing embodiments is a fluoroscopic apparatus, this invention is applicable also to an apparatus other than the fluoroscopic apparatus, such as an X-ray CT apparatus.

(4) The apparatus in the foregoing embodiments is designed for medical use. This invention is applicable not only to such medical apparatus but also to an apparatus for industrial use such as a nondestructive inspecting apparatus.

(5) The apparatus in the foregoing embodiments uses X rays as radiation. This invention is applicable also to an apparatus using radiation other than X rays.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus having radiation emitting means for emitting radiation toward an object under examination, radiation detecting means for detecting radiation transmitted through the object under examination, and signal sampling means for taking radiation detection signals from the radiation detecting means at predetermined sampling time intervals, for obtaining radiographic images based on the radiation detection signals outputted from the radiation detecting means at the predetermined sampling time intervals as radiation is emitted to the object under examination, said apparatus comprising:

time lag removing means for removing lag-behind parts from the radiation detection signals by a recursive computation, on an assumption that a lag-behind part included in each of said radiation detection signals taken at the predetermined sampling time intervals is due to an impulse response formed of a single exponential function or a plurality of exponential functions with different attenuation time constants;

response coefficient to dose relationship storage means for storing, in advance, a relationship of correspondence between impulse response coefficients, which determine conditions relating to the impulse response in the recursive computation performed by said time lag removing means, and radiation doses; and impulse response coefficient setting means for setting an impulse response coefficient corresponding to a radiation dose for the object under examination based on the relationship of correspondence between impulse response coefficients and radiation doses stored in the response coefficient to dose relationship storage means;

wherein said time lag removing means is arranged to obtain corrected radiation detection signals by performing the recursive computation based on the impulse response coefficient set by the impulse response coefficient setting means, to remove the lag-behind parts from the radiation detection signals.

2. A radiographic apparatus as defined in claim 1, wherein said response coefficient to dose relationship storage means is arranged to store, in advance, and as the relationship of correspondence between impulse response coefficients and radiation doses, at least one of a relationship of correspondence between intensities of the exponential function as impulse response coefficients and radiation doses, a relationship of correspondence between attenuation time constants of exponential functions as impulse response coefficients and radiation doses, and a relationship of correspondence between numbers of exponential functions as impulse response coefficients and radiation doses.

3. A radiographic apparatus as defined in claim 1, wherein said time lag removing means is arranged to perform the recursive computation for removing the lag-behind part from each of the radiation detection signals, based on the following equations A–C:

$$X_k = Y_k - \Sigma_{n=1}^{N}\{\alpha_n \cdot [1-\exp(T_n)] \cdot \exp(T_n) \cdot S_{nk}\} \quad \text{A}$$

$$T_n = -\Delta t/\tau_n \quad \text{B}$$

$$S_{nk} = X_{k-1} + \exp(T_n) \cdot S_{n(k-1)} \quad \text{C}$$

where $\Delta t$: the sampling time interval;
- k: a subscript representing a k-th point of time in a sampling time series;
- $Y_k$: an X-ray detection signal taken at the k-th sampling time;
- $X_k$: a corrected X-ray detection signal with a lag-behind part removed from the signal $Y_k$;
- $X_{k-1}$: a signal $X_k$ taken at a preceding point of time;
- $S_{n(k-1)}$: an $S_{nk}$ at a preceding point of time;
- exp: an exponential function;
- N: the number of exponential functions with different time constants forming the impulse response;
- n: a subscript representing one of the exponential functions forming the impulse response;
- $\alpha_n$: an intensity of exponential function n; and
- $\tau_n$: an attenuation time constant of exponential function n; and
- when k=0, $X_0$=0 and $S_{n0}$=0.

4. A radiographic apparatus as defined in claim 1, wherein said impulse response coefficients include intensities of the exponential function, the relationship of correspondence between intensities of the exponential function as impulse response coefficients and radiation doses being derived from a plurality of radiation data actually acquired with conditions of the same irradiation time and gradually differing radiation doses.

5. A radiographic apparatus as defined in claim 1, wherein said impulse response coefficients include intensities of the exponential function, and said impulse response has a plurality of exponential functions, the relationship of correspondence between intensities of the exponential function as impulse response coefficients and radiation doses being stored for each of said exponential functions.

6. A radiographic apparatus as defined in claim 1, wherein said impulse response coefficients include intensities of the exponential function, the relationship of correspondence between intensities of the exponential function as impulse response coefficients and radiation doses being expressed by the following functional equation:

$$\alpha_n = Q \cdot \log W + q$$

where W: X-ray dose;
- Q: gradient of an approximation line indicating the relationship between intensity of the exponential function and X-ray dose; and
- q: section of the approximation line indicating the relationship between intensities of the exponential function and X-ray doses.

7. A radiographic apparatus as defined in claim 1, wherein said response coefficient to dose relationship storage means is a table memory for storing the relationship of correspondence between impulse response coefficients and radiation doses in table form.

8. A radiographic apparatus as defined in claim 1, wherein said radiation detecting means is a flat panel X-ray detector having numerous X-ray detecting elements arranged longitudinally and transversely on an X-ray detecting surface.

9. A radiographic apparatus as defined in claim 1, wherein said apparatus is a medical apparatus.

10. A radiographic apparatus as defined in claim 9, wherein said medical apparatus is a fluoroscopic apparatus.

11. A radiographic apparatus as defined in claim 9, wherein said medical apparatus is an X-ray CT apparatus.

12. A radiographic apparatus as defined in claim 1, wherein said apparatus is for industrial use.

13. A radiographic apparatus as defined in claim 12, wherein said apparatus for industrial use is a nondestructive inspecting apparatus.

14. A radiation detection signal processing method for taking, at predetermined sampling time intervals, radiation detection signals generated by irradiating an object under examination, and performing a signal processing to obtain radiographic images based on the radiation detection signals outputted at the predetermined sampling time intervals, said method comprising the steps of:
- removing lag-behind parts from the radiation detection signals by a recursive computation, on an assumption that a lag-behind part included in each of said radiation detection signals taken at the predetermined sampling time intervals is due to an impulse response formed of a single exponential function or a plurality of exponential functions with different attenuation time constants;
- setting, prior to the above removing step, an impulse response coefficient corresponding to a radiation dose for the object under examination based on a relationship, stored in advance, of correspondence between impulse response coefficients, which determine conditions relating to the impulse response in said recursive computation, and radiation doses; and
- obtaining corrected radiation detection signals by performing the recursive computation, in the above removing step, based on the impulse response coefficient set in the above setting step, to remove the lag-behind parts from the radiation detection signals.

15. A radiation detection signal processing method as defined in claim 14, wherein the recursive computation for removing the lag-behind part from each of the radiation detection signals is performed based on the following equations A–C:

$$X_k = Y_k - \Sigma_{n=1}^{N}\{\alpha_n \cdot [1-\exp(T_n)] \cdot \exp(T_n) \cdot S_{nk}\} \quad \text{A}$$

$$T_n = -\Delta t/\tau_n \quad \text{B}$$

$$S_{nk} = X_{k-1} + \exp(T_n) \cdot S_{n(k-1)} \quad \text{C}$$

where $\Delta t$: the sampling time interval;
- k: a subscript representing a k-th point of time in a sampling time series;
- $Y_k$: an X-ray detection signal taken at the k-th sampling time;
- $X_k$: a corrected X-ray detection signal with a lag-behind part removed from the signal $Y_k$;
- $X_{k-1}$: a signal $X_k$ taken at a preceding point of time;
- $S_{n(k-1)}$: an $S_{nk}$ at a preceding point of time;
- exp: an exponential function;
- N: the number of exponential functions with different time constants forming the impulse response;
- n: a subscript representing one of the exponential functions forming the impulse response;

$\alpha_n$: an intensity of exponential function n; and $\tau_n$: an attenuation time constant of exponential function n; and when k=0, $X_0$=0 and $S_{n0}$=0.

16. A radiation detection signal processing method as defined in claim 14, wherein said impulse response coefficients include intensities of the exponential function, the relationship of correspondence between intensities of the exponential function as impulse response coefficients and radiation doses being derived from a plurality of radiation data actually acquired with conditions of the same irradiation time and gradually differing radiation doses.

17. A radiation detection signal processing method as defined in claim 14, wherein said impulse response coefficients include intensities of the exponential function, the relationship of correspondence between intensities of the exponential function as impulse response coefficients and radiation doses being expressed by the following functional equation:

$$\alpha_n = Q \cdot \log W + q$$

where W: X-ray dose;

Q: gradient of an approximation line indicating the relationship between intensity of the exponential function and X-ray dose; and q: section of the approximation line indicating the relationship between intensities of the exponential function and X-ray doses.

18. A radiation detection signal processing method as defined in claim 14, wherein the relationship of correspondence between impulse response coefficients and radiation doses is stored in table form in a table memory.

19. A radiation detection signal processing method as defined in claim 14, further comprising a step of storing, in advance, the relationship of correspondence between impulse response coefficients and radiation doses.

20. A radiation detection signal processing method as defined in claim 19, wherein said storing step is executed in time of installation or routine adjustment of an apparatus.

* * * * *